(12) United States Patent
Heibel

(10) Patent No.: US 11,179,464 B2
(45) Date of Patent: *Nov. 23, 2021

(54) SYSTEM FOR THE DIRECT PRODUCTION OF THERAPEUTIC YTTRIUM-90 FOR CANCER TREATMENT

(71) Applicant: Westinghouse Electric Company LLC, Cranberry Township, PA (US)

(72) Inventor: Michael D. Heibel, Harrison City, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 90 days.

This patent is subject to a terminal disclaimer.

(21) Appl. No.: 16/274,592

(22) Filed: Feb. 13, 2019

(65) Prior Publication Data

US 2019/0255176 A1    Aug. 22, 2019

Related U.S. Application Data

(60) Provisional application No. 62/631,737, filed on Feb. 17, 2018.

(51) Int. Cl.
| | | |
|---|---|---|
| *A61K 51/00* | (2006.01) | |
| *A61M 36/14* | (2006.01) | |
| *A61K 41/00* | (2020.01) | |
| *A61P 35/00* | (2006.01) | |

(52) U.S. Cl.
CPC .......... *A61K 41/0095* (2013.01); *A61P 35/00* (2018.01); *A61K 41/009* (2013.01)

(58) Field of Classification Search
None
See application file for complete search history.

(56) References Cited

U.S. PATENT DOCUMENTS 6,455,024 B1 * 9/2002 Glajch ................... A61P 35/00
424/1.33
2020/0188689 A1 * 6/2020 Nelson ..................... A61N 5/10

OTHER PUBLICATIONS

G. Jennings et al., "Novel Compact Accelator-Based Neutron and Gamma Sources for Future Detector Calibration," Snowmass 2013 White Paper, 2 pages.

* cited by examiner

*Primary Examiner* — Michael G. Hartley
*Assistant Examiner* — Melissa J Perreira
(74) *Attorney, Agent, or Firm* — K&L Gates LLP

(57) ABSTRACT

Systems and methods including a material that emits high energy beta particles to destroy cancer cells contained in cancerous tumor or tissue. Electronic neutron generators produce neutrons with energies that have a high probability to interact with the material yttrium-89 to produce yttrium-90. Yttrium-90 emits beta radiation with a maximum energy of about 2.25 MeV and a half-life of about 64 hours, which decays to stable zirconium. Stable yttrium-89 can be directly placed in or around cancerous tissue and irradiated with neutrons in the 0.1-15 KeV energy range to produce significant amounts of yttrium-90. The beta radiation emitted by yttrium-90 will primarily destroy the more radiation sensitive cancer cells within the range of the beta particles. The resulting zirconium isotope is not radioactive such that no further radiation is released. A low probability gamma is also created that will assist in cancer cell destruction.

17 Claims, 2 Drawing Sheets

SYSTEM FOR THE DIRECT PRODUCTION OF THERAPEUTIC YTTRIUM-90 FOR CANCER TREATMENT

CROSS-REFERENCE TO RELATED APPLICATION

This application claims priority under 35 U.S.C. § 119(e) to U.S. Provisional Patent Application Ser. No. 62/631,737, filed Feb. 17, 2018, entitled "SYSTEM FOR THE DIRECT PRODUCTION OF THERAPEUTIC YTTRIUM-90 FOR CANCER TREATMENT", which is herein incorporated by reference.

BACKGROUND

1. Field

This invention pertains generally to the treatment of cancer and, more particularly to the treatment of highly localized carcinoma cells.

2. Related Art

The treatment of highly localized carcinoma cells, such as tumors, in the human body using ionizing radiation has proven to be quite effective. However, the application of ionizing radiation to the body typically involves having the radiation pass through healthy tissue before it arrives at the intended target site. This results in damage to the healthy tissue. This limits the amount of damage that can be done to the tumor at one time, resulting in the need for multiple treatments and the accumulating adverse potential biological consequences and financial costs of the treatments. If the healthy cell damage repair does not keep up with the tumor growth rate and/or metastasis rate to allow for sufficient treatment, the victim is likely to perish from the consequences of the carcinoma. Accordingly, a new method of treatment is desired that will attack the cancerous tissue with a minimal effect on the surrounding healthy tissue.

Boron Neutron Capture Therapy (BNCT) has been explored as a possible answer to the foregoing need, however, to date it has been found to lack the therapeutic range of the emitted radiation to be effective. The problem to be solved then is how to take advantage of the neutron generation and application methodology of the BNCT and increase the therapeutic range of the emitted radiation. Thus, there is a need in the art for the design and development of devices capable of emitting radiation in the therapeutic range in accordance with BNCT and methods that employ such devices to effectively treat localized carcinoma cells in an animal, e.g., a patient.

SUMMARY

This invention overcomes the detrimental effects of the radiation treatment of cancer by providing a method of treating localized carcinoma cells in a body of an animal that includes positioning a therapeutic source that is substantially nonradioactive when not exposed to a neutron source or exposed to a neutron source below a given activity level, but becomes a source of highly ionizing but weakly penetrating radiation when exposed to a neutron field at or above the given activity level, within the body in the vicinity of the carcinoma cells. Preferably, positioning of the therapeutic source includes surgically implanting the therapeutic source material on the carcinoma cells. The therapeutic source is irradiated from outside the body with a neutron field at or above the given activity level for a prescribed period of time and the irradiation step is repeated at prescribed intervals. This invention focuses on the design and operation of the therapeutic source as the irradiation target to increase the energy and range of the emitted radiation, such as to achieve a therapeutic range.

In the preferred embodiment, the therapeutic source of highly ionizing but weakly penetrating radiation comprises a thin layer of yttrium metal in which when yttrium-89 absorbs a neutron it transforms to yttrium-90, a medically significant isotope of yttrium, and releases beta radiation with a maximum energy of approximately 2.25 MeV and has a relatively short half-life of 64.1 hours. The layer of yttrium metal is insoluble in water, and non-toxic to the body.

The therapeutic source of highly ionizing but weakly penetrating radiation is configured such that it substantially only irradiates the carcinoma cells. To achieve that end, a radiation shield material is formed on a side of the therapeutic source not facing the carcinoma cells. Preferably, the step of irradiating the therapeutic source includes the step of using an irradiation source, such as an electric neutron generator, e.g., a Neutristor, to irradiate the therapeutic source. One such embodiment employs a plurality of electric neutron generators positioned around the body to irradiate the therapeutic source with a neutron field from different angles.

The method may also include using a neutron moderating material between the electric neutron generator and the therapeutic source to adjust the neutron energy or field to optimize the highly ionizing, but weakly penetrating radiation produced by the therapeutic source. The neutron moderating material may be deuterium oxide ($D_2O$), carbon (C) or other material having similar moderating properties. The neutron moderating material is placed outside the body between the electric neutron generator and the body.

In certain embodiments, the therapeutic source is left within the body between treatments, e.g., intervals, of treating the localized carcinoma cells. The therapeutic source is then removed from the body once the treatments are complete. The therapeutic source may comprise one or more very thin disks or plates with a thickness on the order of a micron, and sufficient combined surface area to ensure the entire volume or area of localized carcinoma cells will be affected by the highly ionizing but weakly penetrating radiation when one or more of the disks or plates are emplaced around the carcinoma cells and irradiated with the neutron field.

The method may also include using a gamma spectrometer to monitor the intensity of gamma radiation emitted as a byproduct of the neutron radiation of the therapeutic source material and the charged particle production rate can be monitored while the neutron irradiation is occurring. The monitored intensity of the gamma radiation and neutron activity of the neutron field can be used to determine the radiation dose that has been applied to the body. The method may also control the intensity of the neutron field based on the monitored gamma intensity and the radiation dose.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENTS

Figure 1:
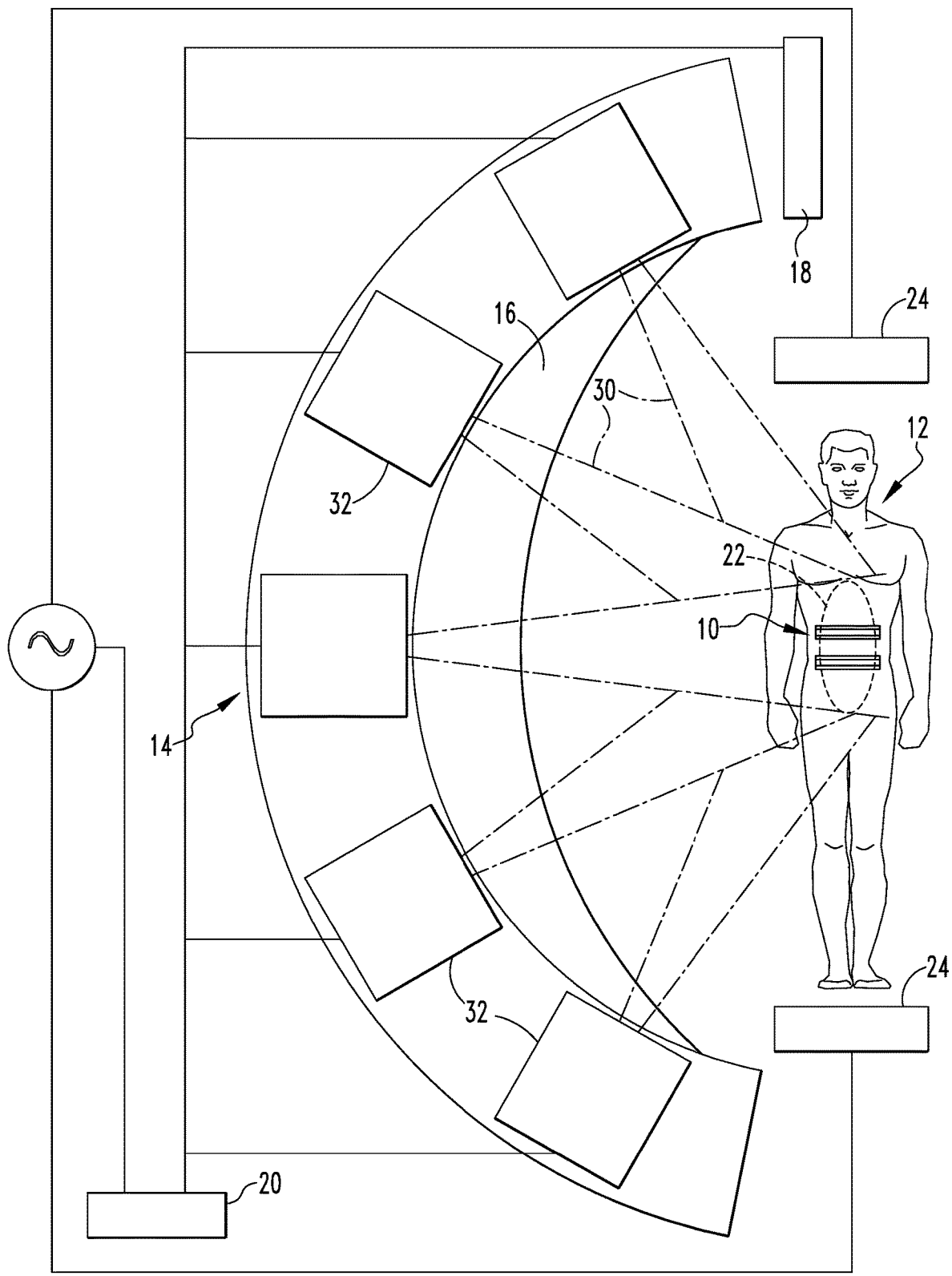
FIG. 1 is a schematic of the apparatus that may be employed to practice the invention, in accordance with certain embodiments.

The invention includes systems and methods for treating localized carcinoma cells, e.g., cancerous tumor(s) and/or tissue, that form and grow in a body of an animal, including a subject, human, person or patient (which terms are using interchangeably herein), which include therapeutic and irradiation/neutron sources. The therapeutic source is positioned or implanted within the body of the patient and, more particularly, in the location or vicinity of target carcinoma cells. In certain embodiments, the therapeutic source is positioned on or adjacent to the target carcinoma cells. The therapeutic source includes one or more devices that include disk(s) or plate(s) or needle(s) having a thickness of about one micron. The one or more disk(s) or plate(s) or needle(s) each or together have sufficient surface area to ensure that the entire volume of the localized carcinoma cells will be affected by emitted radiation. The therapeutic source should be composed or constructed of a material, e.g., metal, that produces high energy alpha or beta particles, and either no energy gamma radiation or low energy gamma radiation. Suitable materials are insoluble in water and non-toxic. The neutron reaction products of the material should also be non-toxic to the patient and have very short half-lives.

The disk(s) or plate(s) or needle(s) may be at least substantially composed or constructed of yttrium, such as in the form of a thin layer or sheet having a thickness of about 1 mm. Natural yttrium is composed of the isotope yttrium-89. Absorption of a neutron by yttrium-89 causes transformation to yttrium-90, which is a medically significant isotope of yttrium useful in radiation treatment of cancer. In general, stable yttrium-89 can be placed in, or on, or around, or in the vicinity of localized cancer cells and irradiated with neutrons in a 0.1-15 KeV energy range to produce a significant amount of yttrium-90 and, in turn, beta radiation emitted by the yttrium-90 can destroy radiation sensitive cancer cells within the range of beta particles. When yttrium-89 absorbs the neutrons, it immediately emits beta radiation with a maximum energy of approximately 2.25 MeV. The beta radiation emitted by yttrium-90 primarily destroys the more radiation sensitive cancer cells within the range of the beta particles. A resulting zirconium isotope is not radioactive and therefore, no further radiation is released. In addition to the beta radiation induced damage to the cancerous tumor or tissue, a low probability gamma is created that assists in cancer cell destruction.

Further, the therapeutic source may include a radiation shield. The metal, e.g., yttrium, layer and the radiation shield may be in a stacked configuration. In positioning the therapeutic source, the surface of the yttrium metal is on the side that faces toward the carcinoma cells and the radiation shield surface is on the opposite side, i.e., a side of the therapeutic source facing away from the carcinoma cells. The radiation shield is composed or constructed of a material that is substantially transparent to neutrons, but can shield at least some of the highly ionizing particles from the healthy tissue surrounding the carcinoma cells. Suitable materials include a light metal such as aluminum, magnesium and alloys thereof, and like materials having relatively low density and similar shielding properties. The presence of the therapeutic shield and configuration/position of the therapeutic source contributes to irradiating only the carcinoma cells, and not irradiating healthy cells.

The therapeutic source, i.e., irradiation target, can be made in many shapes and sizes using commercially available fabrication techniques, to allow them to be placed directly in or adjacent to cancerous cells, tumor(s) and tissue. Since the source is not radioactive unless it has been irradiated by neutrons, there is no personnel radiation exposure occurring while the source is being positioned in or around the patient.

The irradiation/neutron source is positioned outside of the patient body, and may include an electric neutron generator, such as a Neutristor. In general, a suitable irradiation source produces neutrons with energy having a high probability to interact with yttrium-89 to produce yttrium-90. A neutron field emitted by the electric neutron generator irradiates the therapeutic source in the patient body and, in turn, the radiation emitted by the therapeutic source is at a certain activity level, which is within a therapeutic range. The irradiation continues when the electronic neutron generator system is turned off. However, the short range of the emitted beta radiation, and the short decay half-life, 64 hours, ensures that personnel exposure can be easily limited until the irradiated target decays to safe levels. One or more irradiation sources may be employed for a period of time, and repeated at prescribed intervals. A plurality of irradiation sources may be positioned to direct a neutron field toward the patient from different angles. An array of miniature neutron generators can be configured to provide the neutron energy and dose distribution at the site of the therapeutic source, i.e., irradiation target.

In certain embodiments, the array of miniature electrically-powered fast neutron generators is similar in configuration to the "Neutristor" design developed by Sandia National Laboratory and described in a Snowmass 2013 White Paper entitled Novel Compact Accelerator Based Neutron and Gamma Sources for Future Detector Calibration, G. Jennings, C. Sanzeni, D. R. Winn, Fairfield University, Fairfield Conn. 06824, which can be used to irradiate the therapeutic source material with a neutron field once the source material is implanted in the patient. Preferably, the array is configured as necessary to provide a neutron intensity at the therapeutic source position that is sufficient to maximize the neutron reaction rate without providing too much neutron exposure to other parts of the patient's body.

In certain embodiments, the therapeutic source is implanted into the patient body and remains during repeated intervals of radiation treatment. In the time duration between treatments, the therapeutic source is substantially nonradioactive because it is either not exposed to any radiation activity or not exposed to a therapeutic level of radiation activity. Thus, the therapeutic source is controlled to provide treatment to the carcinoma cells only when prescribed or desired. Upon completion of the prescribed number of intervals, the therapeutic source is then removed from the patient body.

Positioned between the irradiation source and the patient body, which contains the therapeutic source, may be a neutron moderator device composed or constructed of a sufficient amount of neutron moderating material such as deuterium oxide ($D_2O$), carbon (C), or any like material having similar moderating properties. The neutron moderator device is placed between each neutron generator and the therapeutic source, and may be independently adjusted to achieve a goal of providing the maximum number of neutrons with an optimum energy for charged particle generation by neutron reactions with the target therapeutic source material. In certain embodiments, a selected neutron energy and/or dose distribution are achieved through a combination of distance from the patient and flexible neutron moderation material, such as a configurable mass of a highly hydrogenous material or various amounts of deuterium contained in a specially configured plastic container.

In certain embodiments, an array of neutron generators is geometrically configured to supply neutron incidents on the carcinoma at different angles to provide the maximum number of sufficiently thermalized neutrons from each generator in the array to reach the target, i.e., therapeutic source, location. This is accomplished through a combination of irradiation/neutron source array geometry and variations in the thickness of the material used as a neutron moderator placed between the neutron array and the therapeutic source, i.e., irradiation target. The calculations required to establish the optimum conditions can be performed by those skilled in the art using a number of different commercially available neutron transport calculation products, such as Monte Carlo N-Particle (MCNP) transport code available from Los Alamos National Laboratory.

The invention may also include a gamma spectrometer that measures the intensity of the gamma radiation emitted by the target isotope created in the neutron reaction so the charged particle production rate can be monitored while the neutron irradiation is occurring. This can be accomplished using a number of commercially available devices.

Also included in the invention, may be computational control system that uses the measured gamma activity and the activity status of the neutron generators to determine radiation dose that has been applied to the patient relative to a dose target. The control system has the ability to increase or decrease the intensity of the neutrons provided by any or all of the neutron generators in the array based on gamma intensity and measured dose measurements.

FIG. 1 is a schematic of a system for the treatment of localized carcinoma cells 22, which may be in the form of cancerous tumor(s) or tissue, in a patient body 12, in accordance with certain embodiments. FIG. 1 includes a therapeutic source 10 implanted inside the patient body 12 and proximate to, and preferably adjacent, the carcinoma cells 22. An irradiation/neutron source 14 is positioned outside of, e.g., spaced a distance from, the patient body 12, and includes an array (e.g., a plurality) of neutron generators 32, which may be miniature in size, that emits a neutron field 30 of neutrons toward the patient body 12. The neutron generators 32 and neutron field 30 emitted therefrom can be configured to provide neutron energy and dose distribution at the site of the therapeutic source 10, i.e., irradiation target. A neutron moderator device 16 is geometrically configured and placed between the array of neutron generators 32 and the patient body 12. A gamma spectrometer 18, a computational control system 20, and an electric field plate 24 are also placed outside of, e.g., spaced a distance from, the patient body 12 in FIG. 1. The gamma spectrometer 18 measures the intensity of the gamma radiation emitted by the therapeutic source 10 as a result of a neutron reaction with a yttrium isotope. The computational control system 20 determines radiation dose that has been applied to the patient body 12 relative to a dose target, and can increase or decrease the intensity of the neutrons provided by any or all of the neutron generators 32 based on gamma intensity and measured dose measurements.

The electric field plate 24 can be provided to accelerate emitted electrons into a penetration depth and/or preferred irradiation direction within the patient body 12. Since beta radiation resembles an electron based on its electrical characteristics, the impact of emitted beta radiation may be further controlled by the application of electric and/or magnetic fields. This approach also allows external electric and/or magnetic fields, e.g., the electric field plate 24, to be manipulated to change the kinetic energy and primary direction of movement of the electrons emitted from the radiator target to better control the applied dose to the patient. As an example, application of an oscillating electric field will allow the radiated electrons to be accelerated beyond, or suppressed from, the range dictated by the kinetic energy imparted by the gamma photon collisions with the gold or platinum electrons. Application of an external magnetic field could be used to concentrate the emitted electron density nearer to or further from the emitter element.

Figure 2:
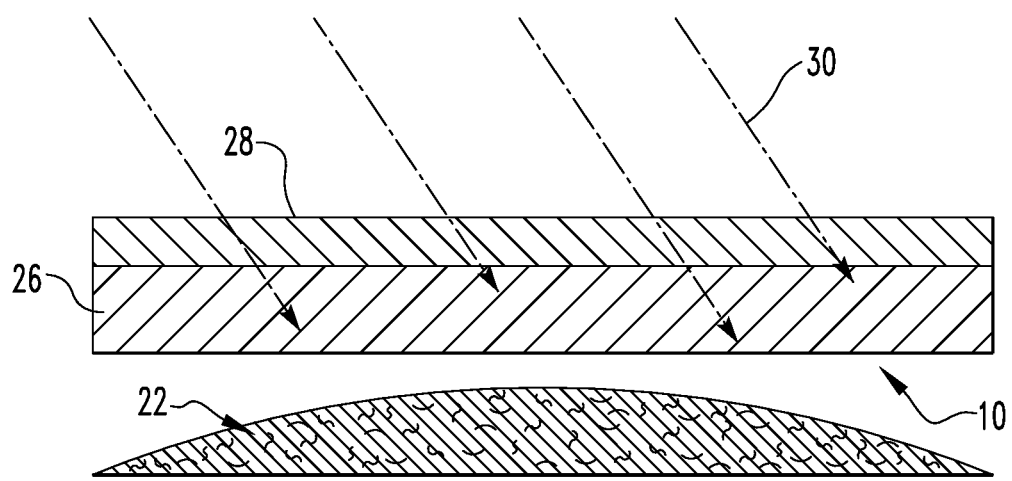
FIG. 2 is a schematic detail of the therapeutic source 10 shown in FIG. 1, in accordance with certain embodiments.

FIG. 2 is a schematic detail of the therapeutic source 10 shown in FIG. 1, in accordance with certain embodiments. FIG. 2 includes a first material 26 and a second material 28. The first material 26 is at least substantially composed of yttrium, which is composed of the isotope yttrium-89, and the second material 28 is representative of a radiation shield, which may be substantially composed of aluminum. One side or surface of the first material 26 is attached to the second material 28, and the other/opposite side or surface of the first material 26 faces the carcinoma cells 22. One side or surface of the second material 28 is attached to the first material 26, and the other/opposite side or surface of the second material 28 faces the neutron field 30 that is generated by the neutron generators 32 (shown in FIG. 1) and interacts with the therapeutic source 10.

Yttrium-90 Beta Radiator Target can be configured in a number of shapes, such as needles or disks, to allow a great deal of therapeutic flexibility.

The methods and systems for treating carcinoma described herein are different from known types of radiation treatments in that they rely on creating and implanting a non-radioactive target in or around a tumor, as compared to the injection of a compound that provides a limited amount of therapeutic treatment deposition in the desired area. The capability of these systems to perform neutron activation of initially non-radioactive materials in, for example, a hospital environment maximizes the benefits of charged particle cancer treatment and minimizes the unwanted expense and radiation exposure to the patient and caregivers. The methods and systems of the invention allow very precise and efficient cancer killing to occur. Additionally, the target source can be left in position, i.e., implanted within a body, without increasing the whole body radiation dose to the patient, until the tumor is completely eliminated. Multiple irradiations can occur with relative ease. The use of the Neutristor neutron generator provides the ability to perform the treatments in a hospital setting instead of a reactor or very large neutron source location. This greatly reduces treatment costs (or greatly increases treatment profitability) relative to existing radiation treatment methods.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A method of treating localized carcinoma cells in a body of an animal comprising the steps of:

positioning a therapeutic source comprising yttrium that has a first radioactivity when not exposed to a neutron source or exposed to a neutron source below a given activity level, and has a second radioactivity greater than the first radioactivity when exposed to a neutron field at or above the given activity level, within the body in a vicinity of the carcinoma cells;

irradiating the therapeutic source from outside the body with a neutron field at or above the given activity level for a prescribed period of time; and repeating the irradiating step at prescribed intervals.

2. The method of treating localized carcinoma cells of claim 1, wherein the therapeutic source is configured to irradiate the carcinoma cells.

3. The method of treating localized carcinoma cells of claim 2, wherein a radiation shield material that is at least partially transparent to neutrons is formed on a side of the therapeutic source not facing the carcinoma cells, shielding at least a portion of the radiation.

4. The method of treating localized carcinoma cells of claim 3, wherein the radiation shield material comprises aluminum.

5. The method of treating localized carcinoma cells of claim 1, wherein the positioning step includes the step of surgically implanting the therapeutic source material on the carcinoma cells.

6. The method of treating localized carcinoma cells of claim 1, wherein irradiating the therapeutic source includes using an electric neutron generator to irradiate the therapeutic source.

7. The method of treating localized carcinoma cells of claim 6, wherein the electric neutron generator comprises a plurality of electric neutron generators positioned around, and outside of, the body to irradiate the therapeutic source from different angles.

8. The method of treating localized carcinoma cells of claim 6, wherein a neutron moderating material is positioned between the electric neutron generator and the therapeutic source to adjust the neutron energy to optimize the radiation produced by the therapeutic source.

9. The method of treating localized carcinoma cells of claim 8, wherein the neutron moderating material comprises deuterium oxide or carbon.

10. The method of treating localized carcinoma cells of claim 1, wherein the therapeutic source remains within the body between treatments of treating the localized carcinoma cells.

11. The method of treating localized carcinoma cells of claim 10, wherein the therapeutic source is removed from the body only when treatment of the localized carcinoma cells is complete.

12. The method of treating localized carcinoma cells of claim 1, wherein the therapeutic source comprises one or more device selected from the group consisting of needle, disk and plate.

13. The method of treating localized carcinoma cells of claim 1, further comprising a gamma spectrometer to monitor the intensity of gamma radiation emitted by a product of the neutron radiation of the therapeutic source material, while a charged particle production rate is monitored while the neutron irradiation occurs.

14. The method of treating localized carcinoma cells of claim 13, wherein the monitored intensity of the gamma radiation and neutron activity of the neutron field is used to determine a radiation dose that has been applied to the body.

15. The method of treating localized carcinoma cells of claim 14, wherein the intensity of the neutron field is controlled based on the monitored gamma intensity and the radiation dose.

16. The method of treating localized carcinoma cells of claim 1, wherein the therapeutic source comprises yttrium-89 that transforms to yttrium-90 when exposed to a neutron field at or above the given activity level.

17. A method comprising:

positioning a therapeutic source comprising yttrium-89 within a body in a vicinity of carcinoma cells;

irradiating the therapeutic source from outside the body with a neutron field to transform at least a portion of the ytrrium-89 into ytrrium-90; and repeating the irradiating step at prescribed intervals.

* * * * *